United States Patent
Sawicka et al.

(10) Patent No.: US 10,328,039 B2
(45) Date of Patent: Jun. 25, 2019

(54) PRODUCTION PROCESS FOR NSAID-CONTAINING LOZENGES, THEIR COMPOSITIONS, THEIR MEDICINAL USE

(75) Inventors: Kirsty Sawicka, Gedling (GB); Jasmine Takhar, Nottingham (GB); Paul Marshall, Deddington (GB); Michael Fanfarillo, Nottingham (GB)

(73) Assignee: RECKITT BENCKISER HEALTHCARE (UK) LIMITED, Slough Berkshire (GB)

( * ) Notice: Subject to any disclaimer, the term of this patent is extended or adjusted under 35 U.S.C. 154(b) by 392 days.

(21) Appl. No.: 11/817,716

(22) PCT Filed: Feb. 27, 2006

(86) PCT No.: PCT/GB2006/000680
§ 371 (c)(1),
(2), (4) Date: Sep. 4, 2007

(87) PCT Pub. No.: WO2006/092569
PCT Pub. Date: Sep. 8, 2006

(65) Prior Publication Data
US 2008/0206326 A1    Aug. 28, 2008

(30) Foreign Application Priority Data
Mar. 1, 2005   (GB) .................................. 0504157.9

(51) Int. Cl.
| | | |
|---|---|---|
| *A61K 31/19* | (2006.01) | |
| *A61K 9/00* | (2006.01) | |
| *A61K 31/192* | (2006.01) | |
| *A61K 45/06* | (2006.01) | |
| *A61K 9/20* | (2006.01) | |

(52) U.S. Cl.
CPC ............ *A61K 31/19* (2013.01); *A61K 9/0056* (2013.01); *A61K 31/192* (2013.01); *A61K 45/06* (2013.01); *A61K 9/2018* (2013.01); *A61K 9/2031* (2013.01)

(58) Field of Classification Search
None
See application file for complete search history.

(56) References Cited

U.S. PATENT DOCUMENTS

| | | | | |
|---|---|---|---|---|
| 5,210,099 A | * | 5/1993 | Mody | .................. A61K 9/0014 |
| | | | | 514/557 |
| 5,360,615 A | * | 11/1994 | Yu et al. | ........................ 424/455 |
| 6,194,003 B1 | * | 2/2001 | Day et al. | ...................... 424/464 |
| 2002/0071857 A1 | | 6/2002 | Kararli et al. | |
| 2007/0190153 A1 | * | 8/2007 | Farber | ........................... 424/488 |

FOREIGN PATENT DOCUMENTS

| | | | |
|---|---|---|---|
| GB | 1 084 864 A | | 9/1967 |
| WO | WO 97/18802 A | | 5/1997 |
| WO | WO 1997/018802 | * | 5/1997 |
| WO | WO 98/52540 A | | 11/1998 |

* cited by examiner

Primary Examiner — Dennis J Parad
Assistant Examiner — Lyndsey M Beckhardt
(74) Attorney, Agent, or Firm — Troutman Sanders LLP; Ryan Schneider; Chris Davis

(57) ABSTRACT

A process for producing a pharmaceutical lozenge formulation comprising the steps of: (a) providing a liquid composition comprising a salt of a non-steroidal anti-inflammatory drug (NSAID salt) and a solvent system, (b) providing a molten lozenge-forming composition, (c) mixing the liquid composition with the molten lozenge-forming composition, and, (d) forming the resulting mixture into lozenges each containing a therapeutically effective amount of said NSAID salt/NSAID mixture. The present application discloses the corresponding NSAID-containing lozenge compositions and their use for the manufacture of a medicament for treating sore throat.

17 Claims, No Drawings

PRODUCTION PROCESS FOR NSAID-CONTAINING LOZENGES, THEIR COMPOSITIONS, THEIR MEDICINAL USE

CROSS REFERENCE TO RELATED APPLICATION

This application is a 35 USC § 371 National Phase Entry Application from PCT/GB2006/000680, filed Feb. 27, 2006, and designating the United States.

The present invention relates to a process for producing a pharmaceutical lozenge formulation and to a pharmaceutical lozenge formulation obtained therefrom.

Pharmaceutical lozenges containing a therapeutically effective amount of a NSAID, for example flurbiprofen, are used in the treatment of sore throats. Suitably, the lozenge is sucked by a patient in need of such treatment and the NSAID is released in the oral cavity and delivered to the surface of the sore throat (i.e. mucous membrane).

Although NSAIDS typically relieve the symptoms associated with a sore throat, NSAIDS typically cause an unpleasant burning sensation at the back of the mouth when retained in the mouth. This is typically clearly unacceptable to the patient being treated. Consequently, processes for producing pharmaceutical lozenges containing a NSAID have been devised where the lozenge formed therefrom relieves the symptoms of a sore throat but the patient does not experience an unacceptable burning sensation.

WO 98/52539 by The Boots Company PLC discloses a process for producing a pharmaceutical lozenge which includes flurbiprofen. The process comprises forming a granular flurbiprofen composition, then mixing the granular composition with a molten lozenge-forming composition, and forming the resulting mixture into lozenges. The resulting lozenges effectively relieve the symptoms of sore throat without producing an unacceptable burning sensation. Typically, however the lozenge formulations include other additional ingredients such as acidity regulators, opacifiers, stabilising agents, buffering agents, flavourings, sweeteners, colouring agents and preservatives. These additional ingredients may be added to the molten lozenge-forming composition, either before or after the flurbiprofen granule has been added thereto. Alternatively, these additional ingredients may be incorporated into the granules. Unexpectedly, it has been found that if such additional ingredients, especially a flavouring, are added to the molten lozenge-forming composition then the resulting lozenge is typically less stable than a comparable lozenge where the additional ingredients, especially a flavouring, are incorporated into the granules.

Suitably, although the incorporation of the additional lozenge ingredients (i.e. flavouring) in a granular component containing the NSAID in a lozenge production process which employs such a granular component may provide a resulting lozenge having an acceptable stability that relieves the symptoms of sore throat without producing an unacceptable burning sensation, in order to produce lozenges having different characteristics and properties using such a lozenge production process it is typically necessary to manufacture separate batches of the granular component, with each respective batch containing the desired additional lozenge ingredients, prior to the lozenge production process. For example, in order to produce lozenges having a different flavour, it is desirable due to stability considerations to produce a first granular component containing the NSAID and a particular flavouring and a separate granular component containing the NSAID and a different flavouring, then to employ each batch in a lozenge production process. Suitably, this is not only inconvenient but it also typically increases the overall cost and complexity of the lozenge production process.

Additionally, when a flavouring is added to a molten lozenge-forming composition it is typically in the form of a liquid (i.e. the flavouring plus an appropriate carrier such as propylene glycol, triacetin, ethanol or essential oils) or it liquefies within the molten lozenge-forming composition. In contrast, when the flavouring is incorporated in a granular component containing the NSAID, the flavouring is typically in the form of a solid (i.e. powder), as it is typically difficult to incorporate liquid flavourings into the granular component. However, due to stability considerations of the resulting lozenge, it is preferable to add the flavouring to the granular component. Unfortunately, however, there are a larger variety of potential flavourings in liquid form than in solid form and flavourings in liquid form typically exhibit a stronger flavour than their solid counterparts. Thus, although a lozenge production process which employs a granular NSAID component may produce lozenges which effectively relieve the symptoms of sore throat without producing an unacceptable burning sensation, such a process typically limits the variety of potential flavourings which may be included in the resulting lozenge and typically limits the strength of the flavour of the resulting lozenge.

The present invention therefore seeks to overcome one or more of the aforementioned technical problems associated with a lozenge production process.

According to a first aspect, the present invention provides a process for producing a pharmaceutical lozenge formulation comprising the steps of:
(a) providing a liquid composition comprising a salt of a non-steroidal anti-inflammatory drug (NSAID salt) and a solvent system;
(b) providing a molten lozenge-forming composition;
(c) mixing the liquid composition with the molten lozenge-forming composition; and
(d) forming the resulting mixture into lozenges each containing a therapeutically effective amount of a NSAID salt/NSAID mixture.

Such a process may be referred to hereinafter as "the process of the present invention".

Typically, the liquid composition comprising the NSAID salt and the solvent system exhibits an acceptable stability, particularly at room temperature and pressure. Conveniently, large batches of the liquid composition may be prepared and stored for use in one or more lozenge production processes at a later date.

Moreover, by employing an NSAID salt in the process of the present invention, the resulting lozenges typically exhibit an acceptable stability when one or more optional ingredients of lozenges i.e. acidity regulators, opacifiers, stabilising agents, buffering agents, sweeteners, flavourings, especially flavourings, are included at any stage of the lozenge production process. Conveniently, it is possible to produce lozenges having different characteristics and properties from a single stock of the liquid composition, merely by dividing the single stock of the liquid composition into a number of batches and using each batch of liquid in a particular lozenge production process. For example, a batch of the liquid composition may be used to produce a lozenge having a particular flavour, and another batch of the liquid composition may be used to produce a lozenge having a different flavour. This may be accomplished merely by changing the flavouring which is included in the lozenge production process. Conveniently, by employing the liquid composition in the process of the present invention, lozenges having different characteristics and properties may be produced without the need for manufacturing separate batches of the liquid composition prior to the lozenge production process.

Conveniently, the use of the liquid composition in the process of the present invention typically increases the flexibility, minimises the complexity and reduces the overall costs of a lozenge production process.

Moreover, the liquid composition, the molten lozenge forming composition, the mixture of the liquid composition and the molten lozenge forming composition used in the process of the present invention and the resulting lozenges formed therefrom typically exhibit an acceptable stability when a flavouring, particularly a liquid flavouring, is added thereto. Conveniently, the use of the NSAID salt in a liquid composition in the process of the present invention typically permits the formation of lozenges having a wider range of flavours compared with lozenges formed by a lozenge production process which uses a granular NSAID component. Furthermore, as flavourings in liquid form typically exhibit a stronger flavour than their powder counterparts, lozenges having a stronger flavour which include substantially less flavouring may be produced by the process of the present invention.

By the term "NSAID salt" as used herein we mean a non-steroidal anti-inflammatory drug in the form of a salt i.e. sodium ibuprofen or sodium flurbiprofen. By the term "NSAID" as used herein we mean a non-steroidal anti-inflammatory drug in the form of a free acid.

Non-steroidal anti-inflammatory drugs (NSAIDS) are a widely used class of medicaments which inhibit cyclooxygenase (Cox), an enzyme involved in the production of prostaglandins (PG). Cox has at least two forms, Cox-1 and Cox-2. Although the term NSAID and NSAID salt as used herein embraces any drug which inhibits any form of cyclooxygenase, preferably the NSAID or salt thereof preferentially inhibits Cox-1 or Cox-2.

Suitable types of NSAIDS which preferentially inhibit Cox-1 may be selected from the following categories:
(1) the propionic acid derivatives;
(2) the acetic acid derivatives;
(3) the fenamic acid derivatives;
(4) the biphenylcarboxylic acid derivatives.

Suitable propionic acid derivatives for use herein include, but are not limited to, ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, and bucloxic acid. Preferred members of the propionic acid group include ibuprofen, naproxen, flurbiprofen, fenoprofen, ketoprofen and fenbufen, especially ibuprofen and flurbiprofen, more especially flurbiprofen.

Suitable acetic acid derivatives for use herein include, but are not limited to, indomethacin, sulindac, tolmetin, zomepirac, diclofenac, fenchlofenac, alchlofenac, ibufenac, isoxepac, furofenac, tiopinac, zidometacin, acemetacin, fentiazac, clidanac and oxipinac. Preferred members of the acetic acid group include tolmetin sodium, zomepinac sodium, sulindac and indomethacin.

The fenamic acid derivatives for use herein include, but are not limited to, mefenamic acid, meclofenamic acid, flufenamic acid, niflumic acid and tolfenamic acid. Preferred members of the fenamic acid group include mefenamic acid and meclofenamic acid.

The biphenylcarboxylic acid derivatives for use herein include, but are not limited to, diflunisal and flufenisal.

Examples of Cox-2 drugs that can be used in the process of the present invention include Etodolac (available from AHP(Shire UK)), Meloxicam (available from Boehringer Ingelheim), Nimesulide (available from Helsinn), Rofecoxib (available from Merck) and Celecoxib (available from Pfizer/Roche). Preferably, the Cox-2 drug is Etodolac or Meloxicam.

Suitably, the NSAIDS for use in the present invention typically exhibit isomerism. Suitably, the term NSAID and NSAID salt embraces all stereoisomers, diastereoisomers, enantiomers and mixtures thereof, including racemic mixtures.

Preferably, the NSAID (and NSAID salt) preferentially inhibits Cox-1. More preferably, the NSAID (and NSAID salt) comprises a propionic acid derivative, in particular an aryl propionic acid derivative, as defined herein. Preferred propionic acid derivatives include naproxen, flurbiprofen, ibuprofen and ketoprofen, particularly racemic mixtures and S-enantiomers thereof. More preferred propionic acid derivatives include flurbiprofen and ibuprofen, particularly racemic mixtures and S-enantiomers. Even more preferred propionic acid derivatives include racemic flurbiprofen and racemic ibuprofen, especially racemic flurbiprofen.

The NSAID in the liquid composition is in the form of a salt (i.e. it is an NSAID salt).

Preferably greater than or equal to 85% by wt, more preferably greater than or equal to 90% by wt, even more preferably greater than or equal to 95% by wt, even more preferably greater than or equal to 97% by wt, even more preferably greater than or equal to 99% by wt of the NSAID, based on the total amount of NSAID in the liquid composition, is in the form of a salt. Most preferably, essentially all of the NSAID in the liquid composition is in the form of a salt.

Preferably, the process of the present invention as defined herein is operated at a pH which is above the pKa of the NSAID. Suitably, the NSAID in the lozenge formed by the process of the present invention is typically in the form of a salt. It will however be appreciated by those skilled in the art that a proportion of the NSAID salt of the liquid composition may be converted to the NSAID (i.e. free acid) during the lozenge production process or a proportion of the NSAID in the liquid composition may be in the form of the free acid. Consequently, the lozenge may contain a therapeutically effective amount of the NSAID salt only or a mixture of said NSAID salt and said NSAID in the form of a free acid. Thus, by the term "a therapeutically effective amount of a NSAID salt/NSAID mixture" in the lozenge we mean that essentially all of the NSAID in the lozenge is in the form of a salt or the lozenge contains a mixture of the NSAID salt and the NSAID in the form of a free acid, such that the total amount of NSAID salt/NSAID mixture in the lozenge is capable of providing a therapeutic effect. Thus, at least a proportion of the NSAID in the lozenge produced by the process of the present invention is in the form of a salt.

Preferably greater than or equal to 20% by weight, more preferably greater than or equal to 30% by wt, even more preferably greater than or equal to 40% by wt, even more preferably greater than or equal to 50% by weight, preferably greater than or equal to 60% by wt, more preferably greater than or equal to 80% by wt, even more preferably greater than or equal to 85% by wt, even more preferably greater than or equal to 90% by wt, even more preferably greater than or equal to 95% by wt, even more preferably greater than or equal to 97% by wt, even more preferably greater than or equal to 99% by wt of the NSAID salt/ NSAID mixture, based on the total amount of said NSAID salt/NSAID mixture in the lozenge formed by the process of the present invention, comprises the NSAID in the form of a salt. Suitably, the balance of the NSAID salt/NSAID mixture, based on the total amount of said NSAID salt/NSAID mixture in the lozenge formed by the process of the present invention, comprises the NSAID in the form of the free acid. Thus, preferably less than or equal to 80% by weight, more preferably less than or equal to 70% by wt, even more preferably less than or equal to 60% by wt, even more preferably less than or equal to 50% by wt, even more preferably less than or equal to 40% by wt, even more preferably less than or equal to 20% by wt, even more preferably less than or equal to 10% by wt, even more preferably less than or equal to 5% by wt, even more preferably less than or equal to 3% by wt, even more preferably less than or equal to 1% by wt of the NSAID salt/NSAID mixture, based on the total amount of said NSAID salt/NSAID mixture in the lozenge formed by the process of the present invention, comprises said NSAID in the form of the free acid.

Most preferably, essentially all of the NSAID in the NSAID salt/NSAID mixture of the lozenge formed by the process of the present invention, based on the total amount of NSAID salt/NSAID mixture in the lozenge, is in the form of a salt.

Preferred NSAID salts include: alkali metal salts (i.e. those elements of Group I of The Periodic Table), especially sodium or potassium; alkaline earth metal salts (i.e. those elements of Group II of The Periodic Table), especially calcium or magnesium; other metal salts, for example aluminium salts; amino acid salts, for example the lysine or arginine salts; or, amine salts, for example meglamine salt.

Preferred salts include the alkali metal salts, the alkaline earth metal salts, amine salts and the amino acid salts. More preferred salts include the alkali metal salts and amino acid salts. Most preferred salts include the alkali metal salts, particularly the sodium or potassium salts, especially the potassium salt.

Suitably, highly preferred NSAID salts for use in the process of the present invention comprise the sodium or potassium salts of the propionic acid derivatives as defined herein, preferably the sodium or potassium salts of racemic ibuprofen or racemic flurbiprofen, more particularly the sodium or potassium salt of racemic flurbiprofen, especially the potassium salt of racemic flurbiprofen.

Suitably, the NSAID salt is present in an amount of greater than or equal to 10% by wt, more preferably greater than or equal to 15% by wt, most preferably greater than or equal to 20% by wt of the liquid composition, based on the total weight of the liquid composition.

Suitably, the NSAID salt is present in an amount of less than or equal to 80% by wt, preferably less than or equal to 75% by wt, more preferably less than or equal to 70% by wt, most preferably less than or equal to 65% by wt of the liquid composition, based on the total weight of the liquid composition.

It will be appreciated by those skilled in the art that the amount of NSAID salt in the liquid composition, and thus the amount of NSAID salt/NSAID mixture in the lozenge formed by the process of the present invention, will depend on, amongst other things, the particular type of NSAID salt employed.

Unit dosages for effective therapy are known to those skilled in the art for each NSAID. For example, they may comprise the NSAID to an extent of 5 mg, 10 mg, 12.5 mg, 25 mg, 50 mg, 100 mg, 150 mg, 200 mg, 250 mg, 300 mg, 350 mg, 400 mg, 500 mg, 600 mg and 800 mg. Where the NSAID salt is employed, as in the process of the present invention, normally the precise unit dosages are chosen to give the equivalent NSAID doses given above.

The therapeutically effective amount of NSAID salt/NSAID mixture in the lozenge formed by the process of the present invention is typically from 5% to 40% of the normal adult dose when given by ingestion to achieve a systemic anti-inflammatory and/or analgesic effect. Flurbiprofen (as the free acid) is typically present in a lozenge formulation in an amount of 2.5 to 20 mg, preferably 5 to 12.5 mg. Ibuprofen (as the free acid) may be present in a lozenge formulation in an amount of 5 to 100 mg, more preferably 10 to 50 mg. Suitably, as the NSAID salt is employed in the process of the present invention, the amount of the salt used should be such as to provide the desired amount of flurbiprofen or ibuprofen as defined above in the resulting lozenge.

Suitably, the NSAID salt/NSAID mixture is typically present in an amount of less than or equal to 10% by weight, more preferably less than or equal to 5% by weight, most preferably less than or equal to 3% by weight of the lozenge formed by the process of the present invention, based on the total weight of the lozenge.

The term "lozenge" as used herein embraces all dosage forms where the product is formed by cooling a sugar-based or sugar alcohol based (e.g. isomalt) molten mass containing the NSAID salt/NSAID mixture. Suitably, the term "molten lozenge-forming composition" embraces a sugar-based or sugar alcohol based (e.g. isomalt) molten mass.

The lozenge is a solid dosage form which is intended to be sucked by a patient. Suitably, the pharmaceutical lozenge formulation including a therapeutically effective amount of NSAID salt/NSAID mixture obtainable by the process of the present invention is intended to be used in the treatment of sore throats by the administration to a patient in need of such treatment. The NSAID salt/NSAID mixture is typically released from the lozenge in the oral cavity thereby delivering the NSAID or salt thereof to the surface of the sore throat. Unexpectedly, an unacceptable burning sensation is typically not experienced when the pharmaceutical lozenge formulations obtained by the process of the present invention are used to treat a sore throat, but the patient does receive relief of the symptoms of the sore throat.

Preferably, the solvent system comprises one or more solvents selected from water, an alcohol, a polyol, a polyether polyol and a derivative of a polyether polyol.

By the term "alcohol" as used herein, we mean an organic molecule which includes a single non-substituted hydroxyl functional group. Preferably, the only functional group present in the alcohol is a non-substituted hydroxyl functional group. Preferred alcohols include ethanol, benzyl alcohol, butanol and propanol, especially ethanol.

By the term "polyol" as used herein, we mean an organic molecule which includes two or more optionally substituted hydroxyl functional groups, provided the polyol derivative includes at least one free (i.e. non-substituted) hydroxyl functional group. Preferably, the polyol includes 2 or 3 hydroxy functional groups. More preferably, the only functional groups present in the polyol are hydroxyl functional groups. Even more preferably, none of the hydroxyl functional groups of the polyol are substituted, namely all of the hydroxyl functional groups are free hydroxyl functional groups. Highly preferred polyols includes propylene glycol (1,2-propanediol), ethylene glycol and glycerol, especially propylene glycol.

By the term "polyether polyol" as used herein, we mean polypropylene glycol, polyethylene glycol and copolymers of polypropylene glycol and polyethylene glycol. Preferably, the polyether polyol is polypropylene glycol or polyethylene glycol, especially polyethylene glycol. The polyether polyol may have a range of molecular weights. Suitable polypropylene glycols have a number average molecular weight (Mn) of 425, 725, 1,000, 2,000, 3,000 and 4,000. Suitable polyethylene glycols have a number average molecular weight (Mn) of 200, 300, 400, 600, 900, 1,000, 1,500, 2,000, 4,600, 8,000, 10,000 and 20,000.

By the term a "derivative of a polyether polyol" as used herein, we mean a polyether polyol as defined herein (i.e. polypropylene glycol, polyethylene glycol and copolymers of polypropylene glycol and polyethylene glycol) wherein one or both of the terminal hydroxyl functional groups of the polyether polyol have been substituted to form a different functional group. Preferred derivatives of polyether polyols include: mono- or di-ethers derivatives wherein one or both terminal hydroxyl groups, respectively, of the polyether polyol have been substituted to form an ether functional group; mono- or di-esters derivatives wherein one or both terminal hydroxyl groups, respectively, of the polyether polyol have been substituted to form an ester functional group; and, mono-ether and mono-ester derivatives wherein one of the terminal hydroxyl groups of the polyether polyol has been substituted to form an ether functional group and the other terminal hydroxyl group of the polyether polyol has been substituted to form an ester functional group. The ether and ester functional groups where possible may also include one or more polyether polyols whose hydroxy functional group may also be substituted. Highly preferred derivatives of polyether polyols include the Tween® group of compounds, for example Tween 20 (polyoxyethylene (20) sorbitan monolaurate), Tween 40 (polyoxyethylene (20) sorbitan monopalmitate), Tween 60 (polyoxyethylene (20) sorbitan monostearate), Tween 80 (polyoxyethylene (20) sorbitan monooleate) and Tween 85 (polyoxyethylene (20) sorbitan trioleate) and the Brij® group of compounds (i.e. polyoxyethylene lauryl ether, polyoxyethylene cetyl ether, polyoxyethylene stearyl ether and polyoxyethylene oleyl ether), for example Brij 30, Brij 35, Brij 52, Brij 56, Brij 58, Brij 72, Brij 76, Brij 78, Brij 92. Most preferred derivatives of polyether polyols are Tween compounds, in particular Tween 20 (polyoxy ethylene (20) sorbitan monolaurate) and Tween 80 (polyoxy ethylene (20) sorbitan monooleate).

According to a preferred embodiment of the process of the present invention, the solvent system comprises two or more solvents as defined herein. Preferably, the solvent system consists essentially of two different solvents as defined herein. By the term the solvent system "consists essentially of two different solvents" we mean said two different solvents represent greater than or equal to 90% by volume, preferably greater than or equal to 95% by volume, more preferably greater than or equal to 97% by volume, even more preferably greater than or equal to 99% by volume of the total volume of the solvents present in the solvent system. Most preferably, the two different solvents represent the only two solvents present in the solvent system.

Similarly, the liquid composition may comprise two or more solvents as defined herein. Preferably, the liquid composition consists essentially of two different solvents as defined herein. By the term "the liquid composition consists essentially of two different solvents" we mean said two different solvents represent greater than or equal to 90% by volume, preferably greater than or equal to 95% by volume, more preferably greater than or equal to 97% by volume, even more preferably greater than or equal to 99% by volume of the total volume of solvents present in the liquid composition. Most preferably, the liquid composition includes two different solvents only.

By the term "different solvents" as used herein in respect of the solvents present in the solvent system and/or liquid composition, we mean the solvent system and/or the liquid composition, accordingly, includes a first solvent which has a different chemical structure than a second solvent. For example, the first solvent may be a polyol as defined herein and the second solvent may be a polyether polyol as defined herein. Alternatively, both the first and second solvents may be of the same generic group e.g. alcohols, wherein the first solvent is propanol and the second solvent is ethanol.

Thus, the solvent system may comprise a first solvent and a second solvent, wherein said first and second solvents are as defined herein. Preferably, said first solvent is different from said second solvent.

Preferably, the first solvent is selected from water, an alcohol, a polyol, a polyether polyol and a derivative of a polyether polyol as defined herein. More preferably, the first solvent comprises an alcohol, a polyol, a polyether polyol and a derivative of a polyether polyol. Even more preferably, the first solvent comprises a polyol, a polyether polyol and a derivative of a polyether polyol, in particular a polyether polyol and a derivative of a polyether polyol, especially a polyether polyol.

Preferably, the second solvent is selected from water, an alcohol, a polyol, a polyether polyol and a derivative of a polyether polyol as defined herein. More preferably, the second solvent comprises water, an alcohol and a polyol, especially water.

Highly preferred solvent systems which comprise a first solvent and a second different solvent include:
(i) a first solvent comprising a polyether polyol, especially polyethylene glycol, and a second solvent comprising water;
(ii) a first solvent comprising a polyether polyol, especially polyethylene glycol, and a second solvent comprising an alcohol, especially ethanol;
(iii) a first solvent comprising a polyether polyol, especially polyethylene glycol, and a second solvent comprising a polyol, especially glycerol or propylene glycol;
(iv) a first solvent comprising a derivative of a polyether polyol, especially a Tween® type compound, and a second solvent comprising water;
(v) a first solvent comprising a derivative of a polyether polyol, especially a Tween® type compound, and a second solvent comprising an alcohol, especially ethanol; and,
(vi) a first solvent comprising a derivative of a polyether polyol, especially a Tween® type compound, and a second solvent comprising a polyol, especially glycerol or propylene glycol.

Of the highly preferred solvent systems listed as (i) to (vi) above, solvent systems (i) to (iii) are typically more preferred than solvent systems (iv) to (vi). The most highly preferred solvent system comprises solvent system (i), in particular a mixture of polyethylene glycol and water.

Preferably, the ratio (% by wt) of the first solvent to the second solvent is typically in the range of 1:5, more preferably 1:3, most preferably 1:2.

In an alternative embodiment of the process of the present invention, the solvent system and/or the liquid composition consists essentially of a single solvent as defined herein. By the term "consists essentially of a single solvent" we mean a single solvent represents greater than or equal to 90% by volume, preferably greater than or equal to 95% by volume, more preferably greater than or equal to 97% by volume, even more preferably greater than or equal to 99% by volume of the total volume of solvents present in the solvent system and/or the liquid composition, respectively. Most preferably, the single solvent represents the only solvent present in the solvent system and/or the liquid composition.

Suitably, when the solvent system and/or the liquid composition consists essentially of a single solvent, said first and second solvents as defined herein are identical i.e. each of the solvents has an identical chemical structure.

Preferably, when the solvent system and/or the liquid composition consists essentially of a single solvent, the single solvent is selected from an alcohol, a polyol, or a polyether polyol as defined herein. More preferably, the single solvent is selected from an alcohol or a polyol, particularly ethanol, propylene glycol or glycerol, especially propylene glycol.

Suitably, the solvent system as defined herein is present in an amount of less than or equal to 90% by wt, preferably less than or equal to 85% by wt, more preferably less than or equal to 80% by wt, even more preferably less than or equal to 75% by wt, even more preferably less than or equal to 70% by wt, even more preferably less than or equal to 65% by wt, most preferably less than or equal to 60% by wt of the liquid composition, based on the total weight of the liquid composition.

Suitably, the solvent system as defined herein is present in an amount of greater than or equal to 20% by wt, preferably greater than or equal to 25% by wt, more preferably greater than or equal to 30% by wt, even more preferably greater than or equal to 35% by wt, even more preferably greater than or equal to 40% by wt of the liquid composition, based on the total weight of the liquid composition.

The liquid composition may be formed by combining the NSAID salt as defined herein with the solvent system as defined herein. Suitably, the NSAID salt in solid form may be combined with the solvent system, preferably with mixing and optionally with heating, to form the liquid composition. Preferably, however, the liquid composition is formed in manner which uses the NSAID itself (i.e. in the form of a free acid).

Thus according to a preferred embodiment of the present invention, the liquid composition is formed by combining a NSAID, a base and the solvent system.

Suitably, the NSAID and the base interact, to form the NSAID salt in the solvent system. The NSAID, base and the solvent system are preferably combined with mixing, and optionally with heating at a temperature up to 100° C. where appropriate.

Suitably, the NSAID, the base and the solvent system may be combined in any order. Thus, the NSAID may be added to the entire solvent system and the base added to the resulting mixture to form the liquid composition or the base may be added to the entire solvent system and the NSAID added to the resulting mixture to form the liquid composition. Alternatively, the base may be added to a portion of the solvent system and the NSAID added to another portion of the solvent system, then the respective portions containing the NSAID and base, respectively, combined to form the liquid composition.

Preferably, the NSAID is added to a portion of the solvent system, the base added to another portion of the solvent system, and then the respective portions containing the NSAID and base, respectively, combined to form the liquid composition.

Thus according to a preferred embodiment of the process of the present invention where the solvent system and/or the liquid composition consists essentially of a single solvent, the NSAID is added to a portion of the single solvent and the base added to another portion of the single solvent, then both of the resulting portions containing the NSAID and base, respectively, are combined to form the liquid composition. More preferably, the portion of the single solvent including the base is added to the other portion of the single solvent which includes the NSAID. As stated hereinbefore, preferably the single solvent is selected from an alcohol, a polyol, or a polyether alcohol, more preferably an alcohol or a polyol, particularly ethanol, propylene glycol or glycerol, especially propylene glycol.

According to another preferred aspect of the process of the present invention where the solvent system and/or the liquid composition comprises two or more solvents as defined herein, particularly where the solvent system and/or liquid composition consists essentially of two different solvents, then the NSAID, the base and the two or more solvents may be combined in any order. For example, the following combinations represent suitable possibilities:

(i) both of the NSAID and base may be added to the first solvent, either simultaneously or sequentially, and then the second solvent added to the resulting mixture to form the liquid composition; or, (ii) the NSAID may be added to the first solvent, the base added to the second solvent, and then the resulting first and second solvent mixtures containing the NSAID and base, respectively, combined to form the liquid composition.

Unexpectedly, it has been found that if the NSAID and base are initially added to a first solvent and then the second solvent added to the resulting mixture (i.e. (i) above), then the mixture of the base, NSAID and first solvent may be difficult to manipulate and/or solvate with the second solvent. In particular, the mixture of the base, NSAID and first solvent may form a viscous semi-solid mass which is difficult to solvate with the second solvent. This effect may be particularly noticeable when the first solvent comprises a polyether polyol or a derivative of a polyether polyol.

Thus preferably, where the solvent system and/or liquid composition comprises two or more solvents as defined herein, the NSAID is added to the first solvent, the base added to the second solvent, and then the resulting first and second solvent mixtures containing the NSAID and base, respectively, are combined to form the liquid composition. More preferably, the second solvent mixture including the base is added to the first solvent mixture which includes the NSAID. Suitably, such a procedure typically eliminates and/or reduces the formation of a viscous solid mass. Conveniently, the liquid composition is typically easier to handle and use in the process of the present invention.

Preferably, the first solvent and second solvents are as defined herein. In particular highly preferred first and second solvent mixtures comprising the NSAID and base respectively include:

(i) a first solvent mixture comprising a NSAID and a first solvent comprising a polyether polyol, especially polyethylene glycol, and a second solvent mixture comprising a base and water;

(ii) a first solvent mixture comprising a NSAID and a polyether polyol, especially polyethylene glycol, and a second solvent mixture comprising a base and an alcohol, especially ethanol;

(iii) a first solvent mixture comprising a NSAID and a polyether polyol, especially polyethylene glycol, and a second solvent mixture comprising a base and a polyol, especially glycerol or propylene glycol;

(iv) a first solvent mixture comprising a NSAID and a derivative of a polyether polyol, especially a Tween® type compound, and a second solvent mixture comprising a base and water;

(v) a first solvent mixture comprising a NSAID and a derivative of a polyether polyol, especially a Tween® type compound, and a second solvent mixture comprising a base and an alcohol, especially ethanol; and (vi) a first solvent mixture comprising a NSAID and a derivative of a polyether polyol, especially a Tween® type compound, and a second solvent mixture comprising a base and a polyol, especially glyercol or propylene glycol.

Of the highly preferred first and second solvent mixtures listed as (i) to (vi) above, solvent mixtures (i) to (iii) are typically more preferred than solvent mixtures (iv) to (vi). The most highly preferred first and second solvent mixture is (i) as detailed above, namely: a first solvent mixture comprising a NSAID and a first solvent comprising a polyether polyol, especially polyethylene glycol, and a second solvent mixture comprising a base and water.

Furthermore, it has also been found that when the solvent system includes two or more solvents, wherein the first solvent comprises a polyether polyol or a derivative of a polyether polyol as defined herein, particularly a polyether polyol (e.g. polyethylene glycol), and a second solvent not including a polyether polyol or a derivative of a polyether polyol, then it is desirable to add the NSAID to the first solvent and the base to the second solvent, rather than adding the base to the first solvent and the NSAID to the second solvent (i.e. the NSAID rather than the base is added to a polyether polyol or a derivative of a polyether polyol when present). Unexpectedly, if the base is added to the polyether polyol or derivative thereof before the NSAID is added thereto, then the polyether polyol or derivative thereof typically discolours and may form an unattractive brown colour. Although only theory, it is possible the inclusion of a base alone may cause a change in the chemical composition of the polyether polyol or derivative thereof i.e. decomposition. Clearly, it is highly undesirable for such reactions to occur.

Thus in order to reduce and/or eliminate such undesirable side reactions, when the solvent system includes a first and second solvents as defined herein, particularly where the first solvent comprises a polyether polyol or a derivative of a polyether polyol and the second solvent does not include a polyether polyol or derivative thereof, a second solvent mixture comprising a base and second solvent is preferably added to a first solvent mixture comprising the NSAID and a first solvent. Preferably, the second solvent comprises water. Conveniently, the amount of free base which may react/interact with the first solvent is typically kept to a minimum/negligible amount as the base preferentially reacts with the NSAID to form the NSAID salt.

Preferably, the liquid composition is in the form of a solution, in particular a colourless solution.

Suitably, where the solvent system comprises two or more solvents, one of which being a polyether polyol or a derivative of a polyether polyol, and the liquid composition is formed by combining a NSAID and a base, then the NSAID is preferentially added to the polyether polyol or a derivative thereof to form a paste and the base added to the second solvent. Preferably, the second solvent comprises an alcohol or water, especially water. Mixing the resulting solvent mixtures, preferably by adding the base and second solvent to the mixture of the NSAID and polyether polyol or derivative thereof, produces the liquid composition typically in the form of a solution.

Preferably, when the liquid composition is formed by combining a NSAID and a base, then the molar ratio of base to NSAID employed in the liquid composition is typically greater than or equal to 0.9 to 1, more preferably greater than or equal to 0.95:1, even more preferably greater than or equal to 0.99:1, most preferably approximately 1:1.

The term "base" embraces any substance which when dissolved in water produces a solution having a pH of greater than 7. Preferred bases include salts of alkali metals (i.e. those elements of Group I of The Periodic Table), especially sodium or potassium, and salts of alkaline earth metals (i.e. those elements of Group II of The Periodic Table), especially calcium or magnesium. Suitable salts of Group I and Group II metals include hydroxide, carbonate and hydrogen carbonate salts, preferably hydroxide. Alternative preferred bases include amines such as ammonia and basic amino acids such as lysine and arginine. Highly preferred bases include sodium hydroxide, potassium hydroxide, lysine and arginine, especially sodium hydroxide and potassium hydroxide. The most preferred base is potassium hydroxide.

If the lozenge-forming composition is sugar based, then it may comprise a single sugar such as sucrose or glucose. Alternatively, the lozenge-forming composition may comprise a mixture of sugars (e.g. a mixture of sucrose and glucose). Preferably, when the lozenge-forming composition is sugar based it comprises a mixture of sugars, especially sucrose and glucose. More preferably, when the lozenge-forming composition comprises a mixture of sucrose and glucose, the ratio by weight of sucrose to glucose in the lozenge-forming composition and the final lozenge is typically in the range of 1:1 to 1:2, preferably 1:1 to 1:1.5.

The sugar based lozenge-forming composition employed in the process of the present invention is preferably in the form of a liquid sugar. By the term "liquid sugar" as used herein, we mean a sugar or mixture of sugars dissolved in an appropriate solvent, preferably the solvent comprises water. Most preferred liquid sugars include liquid glucose, comprising an aqueous solution comprising glucose (e.g. 65 to 90% by wt of sugar solids which includes glucose), and liquid sucrose, comprising an aqueous solution of sucrose (e.g. 55 to 80% by wt sucrose). Suitably, essentially all of the water of the liquid sugar evaporates during the process of the present invention.

If the lozenge-forming composition is sugar alcohol based it may comprise one or more of sorbitol, xylitol, maltitol, lactitol, mannitol, a hydrogenated starch hydrosylate such as maltitol syrup or mixtures thereof, which may be in the form of the free sugar alcohols, derivatives thereof or mixtures thereof. Preferred sugar alcohol based lozenge-forming compositions comprise one or more of sorbitol, maltitol, and a hydrogenated starch hydrosylate or mixtures thereof. More preferred sugar alcohol based lozenge-forming compositions comprise one or more of sorbitol, maltitol and a hydrogenated glucose syrup, namely maltitol syrup which is sold under the Trade Mark Lycasin and typically comprises a mixture of maltitol, sorbitol and hydrogenated oligo- and poly-saccharides. Preferably, the sugar alcohol based lozenge-forming composition consists essentially of one or more sugar alcohols as defined herein. Preferably, the sugar alcohol based lozenge-forming composition essentially does not consist of any sugar.

A preferred sugar alcohol based lozenge-forming composition comprises an approximately equimolar mixture of alpha-D-glucopyranosyl-1,6-D-sorbitol and alpha-D-glucopyranosyl-1,1-D-mannitol (isomalt, which is sold under the trade name of Palatinat®) optionally in conjunction with a hydrogenated glucose syrup such as Lycasin®. An alternative preferred sugar alcohol based lozenge-forming composition comprises a hydrogenated glucose syrup such as Lycasin®. A highly preferred sugar alcohol based lozenge-forming composition comprises a mixture of isomalt and Lycasin® (i.e. isomalt and maltitol syrup).

Preferably, the total weight of a lozenge produced by the process of the present invention is greater than or equal to 1 g, more preferably greater than or equal to 1.5 g, most preferably greater than or equal to 2 g.

Preferably the total weight of a lozenge produced by the process of the present invention is less than or equal to 4 g, more preferably less than or equal to 3.5 g, most preferably less than or equal to 3 g.

Preferably the lozenge-forming composition is present in an amount of greater than or equal to 90% by weight, more preferably greater than or equal to 95% by wt, most preferably greater than or equal to 97% by weight of the lozenge, based on the total weight of the lozenge.

The lozenges may be formed by standard techniques known to those skilled in the art as disclosed in European Patent no. 0862424B (PCT/EP96/05208) by The Boots Company PLC.

For example, lozenges may be formed by heating the lozenge forming composition (e.g. a mixture of sucrose and liquid glucose), preferably under vacuum, to remove excess water. Typically the lozenge forming composition is heated at a temperature in the range of 110 to 175° C., particularly 110 to 150° C. for a sugar based lozenge forming composition and 145 to 175° C. for a sugar alcohol based lozenge forming composition. The liquid composition and any other optional components as described herein are then blended into the molten lozenge forming composition. Suitably, the one or more solvents present in the liquid composition may evaporate during the lozenge production process. The moisture content of the resulting mixture is typically less than or equal to 5% by wt, preferably less than or equal to 4% by wt, more preferably less than or equal to 3% by wt based on the total weight of the mixture. The molten mixture may be passed to individual moulds in which each lozenge is formed or it may be drawn into a continuous cylindrical mass from which the individual lozenges are formed. The lozenges are then cooled, subjected to a visual check and packed into suitable packaging. One form of suitable packaging is a blister pack comprising a water-impermeable plastics material (e.g. polyvinyl chloride) closed by a metallic (e.g. aluminium) foil. The patient may remove the lozenge by applying pressure to the blister to force the lozenge to rupture and pass through the metal foil seal. Lozenges will normally be sucked by the patient to release the NSAID salt/NSAID mixture therefrom.

Lozenges formed by the process of the present invention may also be chewed by the patient. Suitable masticable lozenges may be prepared from an extruded mixture of the liquid composition and the molten lozenge forming composition to which one or more whipping agents, humectants, lubricants, flavourings and colourings have been added (see Pharmaceutical Dosage Forms: Tablets, Volume 1, Second Edition edited by H A Lieberman, L Lachman and J B Schwartz published in 1989).

The lozenges may also contain one or more optional ingredients such as acidity regulators, opacifiers, stabilising agents, buffering agents, flavourings, sweeteners, colouring agents and preservatives. These additional ingredients may be added to the liquid composition, the molten lozenge forming composition, or to the mixture of the liquid composition and the molten lozenge forming composition. Suitably, the total amount of one or more optional ingredients as defined herein present in the lozenge is typically less than or equal to 5% by wt, more preferably less than or equal to 4% by wt, most preferably less than or equal to 3% by wt based on the total weight of the lozenge.

Unexpectedly, the liquid composition comprising a NSAID salt and a solvent system typically exhibits an acceptable stability when one or more of the said optional ingredients as mentioned in the preceding paragraph is added thereto. In particular, the liquid composition, the molten lozenge forming composition, and the mixture of the liquid composition and the molten lozenge forming composition typically exhibit an acceptable stability when a flavouring, particularly a liquid flavouring, is added thereto. Suitably, the resulting lozenges formed by the process of the present invention typically exhibit an acceptable stability when a liquid flavouring is included in the lozenge production process. Suitably, the use of the NSAID salt in the process of the present invention permits the use of both solid and liquid flavourings. Conveniently, as a wider range of suitable flavourings are available in liquid form only, the process of the present invention typically permits the formation of lozenges having a wider range of flavours. Moreover, flavourings in liquid form typically exhibit a stronger flavour than their powder counterparts. Suitably, lozenges having a stronger flavour which include substantially less flavouring may be produced by the process of the present invention.

Thus, according to a further aspect, the process of the present invention further includes the step of including a flavouring, particularly a flavouring in liquid form. The flavouring may be added at any point during the lozenge production process. Suitably, the flavouring may be added to one or more of the liquid composition, the molten lozenge forming composition or the mixture of the liquid composition and the molten lozenge forming composition. Preferably, the flavouring is added to the molten lozenge forming composition and/or the mixture of the liquid composition and the molten lozenge forming composition. Most preferably, the flavouring and the liquid composition are added separately and essentially simultaneously to the molten lozenge forming composition.

Typically, the lozenges prepared by the process of the present invention exhibit an acidic pH when dissolved in water. Preferably, an aqueous solution of a lozenge produced by the process of the present invention has a pH of less than or equal to 6.8, more preferably less than or equal to 6.5, most preferably less than or equal to 6.0. Preferably, an aqueous solution of a lozenge produced by the process of the present invention has a pH of greater than or equal to 5.0, more preferably greater than or equal to 5.5. The acidic pH of the lozenge may arise merely as a consequence of the acidic nature of the components of the lozenge, e.g. the flavouring may be acidic. Preferably, a separate organic acid such as tartaric acid, malic acid or citric acid is not included in the process of the present invention, because the inclusion of such an acid would promote conversion of the NSAID salt to the NSAID.

According to a second aspect of the present invention, there is provided a lozenge obtainable by the process of the present invention.

Preferably, the lozenge comprises a lozenge forming composition as defined herein and a NSAID salt/NSAID mixture as defined herein. More preferably, the lozenge comprises greater than or equal to 95% by weight, more preferably greater than or equal to 97% by wt, of a lozenge forming composition as defined herein and less than or equal to 5% by wt, more preferably less than or equal to 3% by wt, of a NSAID salt/NSAID mixture, based on the total weight of the lozenge. Preferably, the NSAID salt/NSAID mixture comprises the sodium or potassium salt of ibuprofen or the sodium or potassium salt of flurbiprofen, especially the sodium or potassium salt of racemic flurbiprofen. Most preferably, the NSAID salt/NSAID mixture comprises the potassium salt of racemic flurbiprofen.

Preferably, the lozenge further includes a flavouring. Suitably, the flavouring is present in an amount of less than or equal to 3% by wt, more preferably less than or equal to 2% by wt, most preferably less than or equal to 1% by wt of the lozenge based on the total weight of the lozenge.

As mentioned previously, at least some of the components in the mixture of the liquid composition and the molten lozenge-forming composition (i.e. water) may evaporate partially or fully during the lozenge production process. Other higher boiling components (e.g. the polyether polyol and derivatives thereof and polyols when present in the liquid composition) may not evaporate during the lozenge production process. Suitably, the lozenge comprises less than or equal to 5% by wt, more preferably less than or equal to 3% by wt, based on the total weight of the lozenge, of one or more solvents as defined herein. Preferably, the lozenge comprises less than or equal to 3% by wt, more preferably less than or equal to 2% by wt, based on the total weight of the lozenge, of water. Preferably, the lozenge comprises less than or equal to 2% by wt, more preferably less than or equal to 1% by wt, based on the total weight of the lozenge, of a polyol, a polyether polyol or a derivative of a polyether polyol as defined herein, especially a polyether polyol.

Thus according to a third aspect, the present invention provides a pharmaceutical lozenge formulation comprising a therapeutically effective amount of a NSAID salt/NSAID mixture as defined herein contained in a lozenge base formed by cooling a molten lozenge-forming composition as defined herein.

Preferably, the NSAID salt/NSAID mixture is present in an amount of less than or equal to 5% by wt, more preferably less than or equal to 3% by wt based on the total weight of the lozenge. Preferably, the lozenge base (i.e. the cooled molten lozenge-forming composition), is present in an amount of greater than or equal to 95% by wt, more preferably greater than or equal to 97% by wt based on the total weight of the lozenge.

Preferably, the NSAID salt/NSAID mixture comprises the potassium salt of racemic flurbiprofen. Preferably, the NSAID salt/NSAID mixture comprises the potassium salt of racemic flurbiprofen in an amount which is equivalent to 2.5 mg to 20 mg of flurbiprofen free acid.

Preferably, the lozenge includes a flavouring as defined herein.

Preferably, the lozenge includes less than or equal to 5% by wt, more preferably less than or equal to 3% by wt, based on the total weight of the lozenge, of one or more solvents as defined herein.

A highly preferred sugar based lozenge comprises less than or equal to 5% by wt of a NSAID salt/NSAID mixture comprising the potassium salt of racemic ibuprofen contained in greater than or equal to 95% by wt of a lozenge base formed by cooling a molten lozenge-forming composition including glucose or sucrose or a combination thereof, less than or equal to 3% by wt of one or more solvents as defined herein, and less than or equal to 1% by wt of one or more flavourings.

A highly preferred sugar alcohol based lozenge comprises less than or equal to 5% by wt of a NSAID salt/NSAID mixture comprising the potassium salt of racemic ibuprofen contained in greater than or equal to 95% by wt of a lozenge base formed by cooling a molten lozenge-forming composition including isomalt or a hydrogenated glucose syrup or a combation thereof, less than or equal to 3% by wt of one or more solvents as defined herein and less than or equal to 1% by wt of one or more flavourings.

The pharmaceutical lozenge formulations provided by the present invention are compositions which may be sucked by the patient and which typically slowly release the NSAID salt/NSAID mixture. The NSAID salt/NSAID mixture then passes over the mucous membrane of the throat where some is absorbed providing topical relief. The unabsorbed NSAID salt/NSAID mixture is then ingested by the patient and absorbed into the bloodstream. The NSAID salt/NSAID mixture so absorbed can act systemically to provide analgesia, anti-inflammatory and anti-pyretic activity in addition to the relief that comes from the topical application of the NSAID salt/NSAID mixture to the mucous membrane of the throat.

According to a fourth aspect, the present invention provides a lozenge as defined herein or obtainable by the process of the present invention for use in medicine, particularly for treating and/or preventing the symptoms of a sore throat.

Thus according to a fifth aspect of the present invention, there is provided the use of a liquid composition comprising a NSAID salt as defined herein and a solvent system as defined herein and a lozenge forming composition as defined herein in the manufacture of a medicament which releases the NSAID salt/NSAID mixture in the oral cavity so as to deliver the NSAID or salt thereof to the surface of the sore throat.

All features of each aspect of the present invention may be regarded as preferred features of all other aspects of the present invention.

The invention will now be illustrated by means of the following non-limiting examples.

EXAMPLES 1 TO 33: PREPARATION OF A LIQUID COMPOSITION FROM A NSAID AND A BASE

The following liquid compositions of Examples 1 to 33 as detailed in Table 1 were prepared by mixing a NSAID in racemic form with a first solvent, optionally with heating, using a high shear mixer (Silverson L4RT (bench scale) and Silverson AX-3 (factory scale)) to form a first solvent mixture, mixing a base with a second solvent at room temperature to form a second solvent mixture, and then adding the second solvent mixture slowly and with stirring at room temperature to the first solvent mixture. Alternatively, the NSAID may be mixed by hand with the first solvent using a spatula and subsequent mixing steps done by hand for small scale preparations.

In the Examples, where PEG 1000 (Example 16), PEG 8000 (Example 17) and PEG 20000 (Example 23) is used as a first solvent, the PEG is melted prior to addition of flurbiprofen thereto in order to promote dispersion of the flurbiprofen. In Example 24 a small amount of the second solvent (water) was added to the PEG 20000 to promote dispersion of flurbiprofen in the PEG.

In Examples 25 and 26, the first and second solvents are identical and comprise propylene glycol. Thus the liquid composition in these Examples consists of a single solvent only.

In all of Examples 1 to 33, the liquid composition is a stable colourless solution.

TABLE 1

| Example | NSAID (mg) | | First Solvent (mg) | | | | | | | |
|---|---|---|---|---|---|---|---|---|---|---|
| | Flurbiprofen | Ibuprofen | PEG 200 | PEG 300 | PEG 400 | PEG 600 | PEG 1000 | PEG 8000 | PEG 20000 | Tween 20 |
| 1 | 40 | — | — | 25 | — | — | — | — | — | — |
| 2 | 40 | — | — | 20 | — | — | — | — | — | — |
| 3 | 40 | — | — | 15 | — | — | — | — | — | — |
| 4 | 40 | — | — | 13 | — | — | — | — | — | — |
| 5 | 30 | — | — | 25 | — | — | — | — | — | — |
| 6 | 30 | — | — | 25 | — | — | — | — | — | — |
| 7 | 30 | — | — | 25 | — | — | — | — | — | — |
| 8 | — | 40 | — | 25 | — | — | — | — | — | — |
| 9 | — | 50 | — | 20 | — | — | — | — | — | — |
| 10 | — | 60 | — | 15 | — | — | — | — | — | — |
| 11 | — | 60 | — | 10 | — | — | — | — | — | — |
| 12 | 40 | — | — | — | — | — | — | — | — | 25 |
| 13 | 40 | — | — | — | 25 | — | — | — | — | — |
| 14 | 40 | — | — | — | — | 25 | — | — | — | — |
| 15 | 40 | — | 25 | — | — | — | — | — | — | — |
| 16 | 40 | — | — | — | — | — | 25 | — | — | — |
| 17 | 40 | — | — | — | — | — | — | 25 | — | — |
| 18 | 40 | — | — | 12.5 | — | — | — | — | — | — |
| 19 | 40 | — | — | — | — | — | — | — | — | — |
| 20 | 50 | — | — | — | — | — | — | — | — | — |
| 21 | 40 | — | — | — | — | — | — | — | — | — |
| 22 | 40 | — | — | — | — | — | — | — | — | — |
| 23 | 40 | — | — | — | — | — | — | — | 25 | — |
| 24 | 40 | — | — | — | — | — | — | — | 25 | — |
| 25 | 30 | — | — | — | — | — | — | — | — | — |
| 26 | 40 | — | — | — | — | — | — | — | — | — |
| 27 | 40 | — | — | — | — | — | — | — | — | — |
| 28 | 40 | — | — | — | 54 | — | — | — | — | — |
| 29 | 40 | — | — | — | 54 | — | — | — | — | — |
| 30 | 40 | — | — | — | 44 | — | — | — | — | — |
| 31 | 40 | — | — | — | 42 | — | — | — | — | — |
| 32 | 40 | — | — | — | 40 | — | — | — | — | — |
| 33 | 40 | — | — | 29 | — | — | — | — | — | — |

| Example | First Solvent (mg) | | Base (mg) | | Second Solvent (mg) | | | |
|---|---|---|---|---|---|---|---|---|
| | Tween 80 | Propylene Glycol | Potassium hydroxide | Sodium hydroxide | Water | Glycerol | Ethanol | Propylene Glycol |
| 1 | — | — | 10 | — | 25 | — | — | — |
| 2 | — | — | 10 | — | 30 | — | — | — |
| 3 | — | — | 10 | — | 35 | — | — | — |
| 4 | — | — | 10 | — | 37 | — | — | — |
| 5 | — | — | 7.5 | — | — | 37.5 | — | — |
| 6 | — | — | 7.5 | — | — | 37.5 | — | — |
| 7 | — | — | 7.5 | — | — | — | 37.5 | — |
| 8 | — | — | 10 | — | 25 | — | — | — |
| 9 | — | — | 10 | — | 20 | — | — | — |
| 10 | — | — | 10 | — | 15 | — | — | — |
| 11 | — | — | 10 | — | 20 | — | — | — |
| 12 | — | — | 10 | — | 25 | — | — | — |

TABLE 1-continued

| Example | | | | | | | | |
|---|---|---|---|---|---|---|---|---|
| 13 | — | — | 10 | — | 25 | — | — | — |
| 14 | — | — | 10 | — | 25 | — | — | — |
| 15 | — | — | 10 | — | 25 | — | — | — |
| 16 | — | — | 10 | — | 25 | — | — | — |
| 17 | — | — | 10 | — | 25 | — | — | — |
| 18 | — | 12.5 | 10 | — | 25 | — | — | — |
| 19 | — | 25 | 10 | — | 25 | — | — | — |
| 20 | — | 13 | 13 | — | 24 | — | — | — |
| 21 | — | 20 | 10 | — | 30 | — | — | — |
| 22 | — | 10 | 10 | — | 40 | — | — | — |
| 23 | — | — | 10 | — | 25 | — | — | — |
| 24 | — | — | 10 | — | 25 | — | — | — |
| 25 | — | 31 | 7.5 | — | — | — | — | 31 |
| 26 | — | 25 | 10 | — | — | — | — | 25 |
| 27 | 25 | — | 10 | — | 25 | — | — | — |
| 28 | — | — | — | 2 | 4 | — | — | — |
| 29 | — | — | 2 | — | 4 | — | — | — |
| 30 | — | — | 8 | — | 8 | — | — | — |
| 31 | — | — | 9 | — | 9 | — | — | — |
| 32 | — | — | 10 | — | 10 | — | — | — |
| 33 | — | — | 10 | — | 21 | — | — | — |

EXAMPLES 34 TO 37: PREPARATION OF A LIQUID COMPOSITION FROM A NSAID SALT

The following liquid compositions of Examples 34 to 37 as detailed in Table 2 were prepared by mixing the NSAID salt in racemic form with the solvent system at room temperature using a high shear mixer.

TABLE 2

| | NSAID salt (mg) | | Solvent System (mg) | | |
|---|---|---|---|---|---|
| Example | Sodium ibuprofen | Potassium flurbiprofen | Water | Propylene Glycol | Ethanol |
| 34 | 50 | — | 25 | 25 | — |
| 35 | 60 | — | 20 | — | 30 |
| 36 | — | 40 | 20 | 30 | — |
| 37 | — | 35 | 15 | — | 35 |

EXAMPLES 38 TO 45: PRODUCTION OF SUGAR BASED LOZENGES

Sugar based lozenges are prepared by heating a mixture of sugar (sucrose) and liquid glucose (80 wt % sugar solids including glucose and 20% by wt water) containing approximately an equal weight of sucrose and sugar solids from liquid glucose to a temperature of 140° C. and applying a vacuum to reduce the water content of the mixture. The appropriate amount of the liquid composition of Examples 1 to 37 is blended into the molten sugar and glucose mixture, the resulting mixture cooled and formed into a continuous cylindrical mass from which lozenges are formed. The individual lozenges are inspected visually and then packed.

Optional ingredients, such as acidity regulators, opacifiers, stabilising agents, buffering agents, flavourings, sweeteners, colouring agents and preservatives may be added to one or more of the liquid composition, the molten sucrose and glucose mixture, or the mixture of the liquid composition and the molten sucrose and glucose mixture. Preferably, the flavouring is added to the molten sugar and glucose mixture at the same time the liquid composition is added to the molten sugar and glucose mixture.

In this manner lozenges were prepared containing the following ingredients expressed as the weight in milligrammes per lozenge.

| | Ex. 38 | Ex. 39 | Ex. 40 | Ex. 41 | Ex. 42 | Ex. 43 | Ex. 44 | Ex. 45 |
|---|---|---|---|---|---|---|---|---|
| Racemic flurbiprofen potassium salt | 10.93 | 10.93 | 6.24 | 3.12 | 15.61 | — | — | — |
| Racemic ibuprofen potassium salt | — | — | — | — | — | 15 | 25 | 30 |
| PEG 1000 | 5.469 | — | — | — | 7.81 | — | — | — |
| PEG 8000 | — | 5.469 | — | — | — | — | — | — |
| PEG 300 | — | — | 3.12 | — | — | 2.5 | 4.16 | 5.0 |
| PEG 600 | — | — | — | 1.56 | — | — | — | — |
| Flavouring (cherry) | 5.0 | 5.0 | 5.0 | 5.0 | 5.0 | 5.0 | 5.0 | 5.0 |
| Flavouring (levomenthol) | 2.0 | 2.0 | 2.0 | 2.0 | 2.0 | 2.0 | 2.0 | 2.0 |
| Carmosine (E122) | 0.4 | 0.4 | 0.4 | 0.4 | 0.4 | 0.4 | 0.4 | 0.4 |
| Water | Trace | Trace | Trace | Trace | Trace | Trace | Trace | Trace |
| Solids from a 1:1 mixture of sugar and liquid glucose | Balance to 2500 | Balance to 2500 | Balance to 2500 | Balance to 2500 | Balance to 2500 | Balance to 2500 | Balance to 2500 | Balance to 2500 |

Examples 38 and 42 were prepared from the liquid composition of Example 16, Example 39 prepared from the liquid composition of Example 17, Example 40 prepared from the liquid composition of Example 1, Example 41 prepared from the liquid composition of Example 14, and Examples 43 to 45 prepared from the liquid composition of Example 11. The flavourings cherry (15061357 from International Flavors & Fragrances) and levomenthol (Fuerst Day Lawson Ltd) are liquid flavourings and were added to the liquid composition. The resulting lozenges were found to provide a palatable, stable and effective treatment for sore throats.

EXAMPLES 46 TO 53: PRODUCTION OF SUGAR ALCOHOL BASED LOZENGES

The sugar alcohol based lozenges are prepared in the same manner as the sugar based lozenges except the mixture of sugar and liquid glucose is replaced with isomalt dissolved in the minimum amount of water, and where appropriate lycasin also added. The resulting mixture is heated to 170° C. and the liquid composition and other optional components added thereto.

In this manner lozenges were prepared containing the following ingredients expressed as the weight in milligrammes per lozenge.

|  | Ex. 46 | Ex. 47 | Ex. 48 | Ex. 49 | Ex. 50 | Ex. 51 | Ex. 52 | Ex. 53 |
|---|---|---|---|---|---|---|---|---|
| Racemic flurbiprofen potassium salt | 10.93 | 10.93 | 6.24 | 3.12 | 15.61 | — | — | — |
| Racemic ibuprofen potassium salt | — | — | — | — | — | 15 | 25 | 30 |
| PEG 1000 | 5.469 | — | — | — | 7.81 | — | — | — |
| PEG 8000 | — | 5.469 | — | — | — | — | — | — |
| PEG 300 | — | — | 3.12 | — | — | 2.5 | 4.16 | 5.0 |
| PEG 600 | — | — | — | 1.56 | — | — | — | — |
| Flavouring (cherry) | 5.0 | 5.0 | 5.0 | 5.0 | 5.0 | 5.0 | 5.0 | 5.0 |
| Flavouring (levomenthol) | 2.0 | 2.0 | 2.0 | 2.0 | 2.0 | 2.0 | 2.0 | 2.0 |
| Isomalt | 2325 | 1885 | 1885 | 1885 | 2325 | 1885 | 2325 | 1885 |
| Water | Trace | Trace | Trace | Trace | Trace | Trace | Trace | Trace |
| Lycasin | — | 440 | 440 | 440 | — | 440 | — | 440 |

Examples 46 and 50 were prepared from the liquid composition of Example 16, Example 47 prepared from the liquid composition of Example 17, Example 48 prepared from the liquid composition of Example 1, Example 49 prepared from the liquid composition of Example 14, and Examples 51 to 53 prepared from the liquid composition of Example 11. The flavourings Cherry (15061357) from International Flavors & Fragrances and levomenthol from Fuerst Day Lawson Ltd are liquid flavourings and were included in the liquid composition.

The resulting lozenges were found to provide a palatable, stable and effective treatment for sore throats.

EXAMPLES 54 TO 59: DISCOLOURATION OF POTASSIUM HYDROXIDE AND POLYETHER POLYOL MIXTURES

The following liquid compositions as detailed in Table 3 were prepared by forming a mixture of potassium hydroxide (KOH) and the appropriate polyether polyol (Tween® 80, Tween® 20, PEG 300) and optionally including water, ethanol or glycerol. Where water, ethanol or glycerol is present the potassium hydroxide is initially dissolved in one of these solvents at room temperature with stirring and then the resulting solution mixed with the polyether polyol. When the polyether polyol is the only solvent in the liquid composition then the potassium hydroxide is added directly to the polyether polyol with stirring. The colour change of each solution was observed over 24 hours at room temperature.

TABLE 3

| Example | Water (ml) | Glycerol (ml) | Ethanol (ml) | PEG 300 (ml) | Tween 20 (ml) | Tween 80 (ml) | KOH (mg) | Comments |
|---|---|---|---|---|---|---|---|---|
| 54 | 16.6 | — | — | 66.6 | — | — | 16.6 | After 1 hour the solution turned yellow and eventually turned a dark brown colour after 24 hours. |
| 55 | — | 53.6 | — | 35.7 | — | — | 10.7 | The solution turned a yellow colour after 24 hours |
| 56 | — | — | 53.6 | 35.7 | — | — | 10.7 | The solution turned a yellow colour after 1 hour and eventually turned a dark brown/orange colour after 24 hours. |
| 57 | — | 41.7 | — | 41.7 | — | — | 16.7 | A dark brown viscous solution formed almost immediately. |

TABLE 3-continued

| Example | Water (ml) | Glycerol (ml) | Ethanol (ml) | PEG 300 (ml) | Tween 20 (ml) | Tween 80 (ml) | KOH (mg) | Comments |
|---|---|---|---|---|---|---|---|---|
| 58 | — | — | — | — | 71.4 | — | 28.6 | A dark brown viscous solution formed almost immediately. |
| 59 | — | — | — | — | — | 71.4 | 28.6 | A dark brown viscous solution formed almost immediately. |

The results in Table 3 demonstrate that when potassium hydroxide is added to a polyether polyol in the absence of a NSAID then the resulting liquid composition may discolour thereby suggesting the resulting liquid composition may be unstable.

In contrast, as demonstrated by Examples 1 to 33, the resulting liquid composition formed by initially adding a NSAID to a polyether polyol and then adding a base thereto typically forms a stable colourless solution.

EXAMPLES 60 TO 64: STABILITY STUDIES OF LIQUID COMPOSITIONS COMPRISING A NSAID SALT

The following liquid compositions as detailed in Table 4 were prepared by mixing racemic flurbiprofen with polyethylene glycol 400 (PEG 400) at room temperature by hand to form a paste. A second aqueous solution comprising a base (potassium hydroxide or sodium hydroxide) was added to the paste comprising racemic flurbiprofen and PEG 400 with stirring at room temperature to form a colourless solution. Each of the liquid compositions remained as a colourless solution when stored at room temperature for 24 hours.

TABLE 4

Liquid Compositions comprising a NSAID salt

| Example | Flurbiprofen (mg) | PEG 400 (ml) | Water (ml) | Sodium hydroxide (mg) | Potassium hydroxide (mg) |
|---|---|---|---|---|---|
| 60 | 40 | 54 | 4 | 2 | — |
| 61 | 40 | 54 | 4 | — | 2 |
| 62 | 40 | 44 | 8 | — | 8 |
| 63 | 40 | 42 | 9 | — | 9 |
| 64 | 40 | 40 | 10 | — | 10 |

EXAMPLES 65 TO 67: STABILITY STUDIES OF LIQUID COMPOSITION COMPRISING A NSAID SALT AND A FLAVOURING

A liquid composition including a flavouring (Example 65) was prepared by adding levomenthol (Fuerst Day Lawson Ltd) to the liquid composition as detailed in Example 60 so the resulting solution comprised an amount equivalent to 87.5 mg of flurbiprofen and 100 mg of levomenthol. In a similar manner, liquid compositions including a flavouring referred to as Examples 66 and 67 were prepared comprising an amount equivalent to 87.5 mg of flurbiprofen and 100 mg of levomenthol by adding levomenthol to the appropriate amount of the liquid compositions of Examples 61 and 62, respectively. The resulting liquid compositions including levomenthol (Examples 65 to 67) were stored at 50° C. for 14 days in glass bottles and then analysed by HPLC to detect any decomposition products, in particular flurbiprofen-menthyl ester. The results are presented in Table 5.

TABLE 5

| | Detection of flurbiprofen-menthyl ester | |
|---|---|---|
| Example | Menthyl ester after 7 days at 50° C. | Menthyl ester after 14 days at 50° C. |
| 60 | 0.30% | 0.58% |
| 61 | 0.55% | 0.99% |
| 62 | 0.02% | 0.04% |

The results indicate that a liquid composition comprising flurbiprofen and a flavouring exhibit an acceptable stability as only trace amounts of the decomposition product were detected.

EXAMPLES 68 TO 70: STABILITY STUDIES OF LOZENGES COMPRISING FLURBIPROFEN AND A FLAVOURING

A sugar based lozenge referred to as Example 68 was prepared according to the procedure as detailed in Examples 38 to 45 employing the liquid composition as detailed in Example 62 including levomenthol (Fuerst Day Lawson Ltd) as a flavouring, so that the resultant lozenge included a NSAID salt/NSAID mixture in an amount equivalent to 8.75 mg of flurbiprofen free acid and 8 mg of levomenthol. In a similar manner, lozenges referred to as Examples 69 and 70 were prepared from liquid compositions of Examples 63 and 64, respectively, so that the resultant lozenges of these Examples also included a NSAID salt/NSAID mixture in an amount equivalent to 8.75 mg of flurbiprofen free acid and 8 mg of levomenthol.

The lozenges were stored at 40° C. and 50° C. for 28 days and then analysed by HPLC to detect any decomposition products, in particular flurbiprofen-menthyl ester and polyethylene glycol esters (PEG esters). The results are presented in Table 6.

TABLE 6

| | Immediately after manufacture | | 28 days at 40° C. | | 28 days at 50° C. | |
|---|---|---|---|---|---|---|
| Example | Flurbiprofen-menthyl ester | PEG esters | Flurbiprofen-menthyl ester | PEG esters | Flurbiprofen-menthyl ester | PEG esters |
| 68 | None | None | 0.27% | None | 1.20% | 0.37% |
| 69 | None | None | 0.10% | None | 0.39% | 0.40% |
| 70 | None | None | None | None | 0.11% | 0.14% |

The results in Table 6 indicate that lozenges including a flavouring produced by the process of the present invention exhibit an acceptable stability.

The invention claimed is:

1. A process for producing a pharmaceutical lozenge formulation comprising:
    providing a liquid composition comprising a salt of a non-steroidal anti-inflammatory drug (NSAID salt), a base, and a solvent system, the solvent system comprising two or more solvents including at least a first solvent and a second solvent, wherein the first solvent comprises polyethylene glycol or a derivative of polyethylene glycol, wherein the second solvent of the solvent system is selected from the group consisting of water, an alcohol and a polyol, and wherein the first solvent is different than the second solvent;
    providing a molten lozenge-forming composition;
    mixing the liquid composition with the molten lozenge-forming composition; and,
    forming the resulting mixture into lozenges each containing a therapeutically effective amount of a NSAID salt the NSAID comprising flurbiprofen,
    wherein the NSAID salt is present in an amount of less than or equal to 5% by weight of each lozenge;
    wherein the polyethylene glycol or derivative of polyethylene glycol has a molecular weight of 200, 300, 400, 600, or 900; and
    wherein providing the liquid composition comprises:
    mixing the NSAID with the first solvent to form a first solvent mixture at room temperature;
    mixing the base with the second solvent to form a second solvent mixture; and
    mixing the first solvent mixture with the second solvent mixture to form the liquid composition.

2. A process as claimed in claim 1 further comprising including a flavoring in one or more of the liquid composition, the molten lozenge-forming composition or the mixture of the liquid composition and the molten lozenge-forming composition.

3. A process as claimed in claim 1, wherein the NSAID salt comprises a Group 1 metal salt of the NSAID, a Group II metal salt of the NSAID, or an amino acid salt of the NSAID.

4. A process as claimed in claim 3, wherein the NSAID salt comprises the sodium or potassium salt of the NSAID.

5. A process as claimed in claim 1, wherein the molten lozenge-forming composition comprises a mixture of sucrose and glucose.

6. A process as claimed in claim 1, wherein the molten lozenge-forming composition comprises one or more of sorbitol, xylitol, maltitol, a hydrogenated starch hydrosylate, lactitol, mannitol or derivatives thereof.

7. A process as claimed in claim 1, wherein the molten lozenge-forming composition comprises an approximately equimolar mixture of alpha-D-glucopyranosyl-1,6-D-sorbitol and alpha-D-glucopyranosyl-1,1-D-mannitol.

8. A process as claimed in claim 1, wherein the molten lozenge-forming composition comprises a hydrogenated glucose syrup.

9. A process as claimed in claim 1, wherein the second solvent comprises water.

10. A process as claimed in claim 1, wherein the NSAID salt comprises a Group 1 metal salt of the NSAID.

11. A process as claimed in claim 1, wherein greater than or equal to 90% by wt of the NSAID, based on the total amount of NSAID in the liquid composition, is in the form of a salt.

12. A process as claimed in claim 1, wherein greater than or equal to 95% by wt of the NSAID, based on the total amount of NSAID in the liquid composition, is in the form of a salt.

13. A process as claimed in claim 1, wherein greater than or equal to 97% by wt of the NSAID, based on the total amount of NSAID in the liquid composition, is in the form of a salt.

14. A process as claimed in claim 1, wherein greater than or equal to 99% by wt of the NSAID, based on the total amount of NSAID in the liquid composition, is in the form of a salt.

15. A process as claimed in claim 1, wherein the molten lozenge-forming composition comprises one or more sugars.

16. A process as claimed in claim 1, wherein the molten lozenge-forming composition comprises one or more sugar alcohols.

17. A process as claimed in claim 1, wherein 85%-95% by wt of the NSAID, based on the total amount of NSAID in the liquid composition, is in the form of a salt.

* * * * *

UNITED STATES PATENT AND TRADEMARK OFFICE
CERTIFICATE OF CORRECTION

PATENT NO. : 10,328,039 B2
APPLICATION NO. : 11/817716
DATED : June 25, 2019
INVENTOR(S) : Kirsty Sawicka et al.

It is certified that error appears in the above-identified patent and that said Letters Patent is hereby corrected as shown below:

On the Title Page

At (73) Assignee, please replace "Reckiit Benckiser Healthcare (UK) Limited" with - Reckitt Benckiser Healthcare (UK) Limited -

Signed and Sealed this
Twentieth Day of August, 2019

Andrei Iancu
*Director of the United States Patent and Trademark Office*